(12) United States Patent
Shaker

(10) Patent No.: US 6,773,452 B2
(45) Date of Patent: Aug. 10, 2004

(54) MANOMETRY APPARATUS FOR MEASURING ESOPHAGEAL SPHINCTER COMPLIANCE

(75) Inventor: Reza Shaker, Brookfield, WI (US)

(73) Assignee: Wilson-Cook Medical Incorporated, Winston-Salem, NC (US)

( * ) Notice: Subject to any disclaimer, the term of this patent is extended or adjusted under 35 U.S.C. 154(b) by 429 days.

(21) Appl. No.: 09/818,181

(22) Filed: Mar. 27, 2001

(65) Prior Publication Data

US 2001/0053920 A1 Dec. 20, 2001

Related U.S. Application Data

(60) Provisional application No. 60/192,172, filed on Mar. 27, 2000.

(51) Int. Cl.[7] ............................................. A61B 18/18
(52) U.S. Cl. .................. 606/587; 600/593; 604/101.05; 128/898
(58) Field of Search ................................ 600/380, 593, 600/546, 587, 373, 29; 607/40, 133; 128/898; 606/191, 192, 196, 198, 199, 159; 604/264, 101.01, 102.01, 103.03, 103.12, 96.01, 97.02, 104, 173, 101.05

(56) References Cited

U.S. PATENT DOCUMENTS

| | | | |
|---|---|---|---|
| 3,046,988 A | | 7/1962 | Moreau et al. |
| 4,640,298 A | | 2/1987 | Pless et al. |
| 4,643,192 A | * | 2/1987 | Fiddian-Green ............ 600/366 |
| 4,809,710 A | * | 3/1989 | Williamson ................. 600/561 |
| 4,887,610 A | | 12/1989 | Mittal |
| 5,314,409 A | * | 5/1994 | Sarosiek et al. ........ 604/101.03 |
| 5,433,216 A | * | 7/1995 | Sugrue et al. .............. 600/591 |
| 5,551,425 A | | 9/1996 | Essen-Moller |
| 5,551,439 A | * | 9/1996 | Hickey ....................... 600/486 |
| 5,718,685 A | * | 2/1998 | Roewer et al. ......... 604/100.01 |
| 5,924,984 A | | 7/1999 | Rao |
| 6,021,781 A | | 2/2000 | Thompson et al. |
| 6,097,984 A | | 8/2000 | Douglas |
| 6,334,064 B1 | * | 12/2001 | Fiddian-Green ............ 600/311 |
| 6,589,238 B2 | * | 7/2003 | Edwards et al. .............. 606/41 |

FOREIGN PATENT DOCUMENTS

| | | |
|---|---|---|
| EP | 0149866 | 7/1985 |
| WO | 9100752 | 1/1991 |

* cited by examiner

Primary Examiner—Henry Bennett
Assistant Examiner—Kathryn Odland
(74) Attorney, Agent, or Firm—Charles W. Agnew

(57) ABSTRACT

An apparatus and method for measuring the compliance of the lower esophageal sphincter (LES), the apparatus including a catheter having a plurality of extendable members for both measuring the compliance of the LES and stimulating the esophagus which relaxes the LES to obtain a more clinically relevant measurement of LES compliance. In one embodiment, the plurality of extendable members include a first balloon which is located and inflated within the esophagus to trigger esophageal motility, a second, non-elastic balloon that is positioned within the LES, and a third balloon which is inflated within the stomach to help align the second balloon with LES. Incrementally increasing volumes of air are introduced into the second balloon, with the resulting pressures exerted by the LES calculated and compared to normative values to assess the condition of the LES.

17 Claims, 6 Drawing Sheets

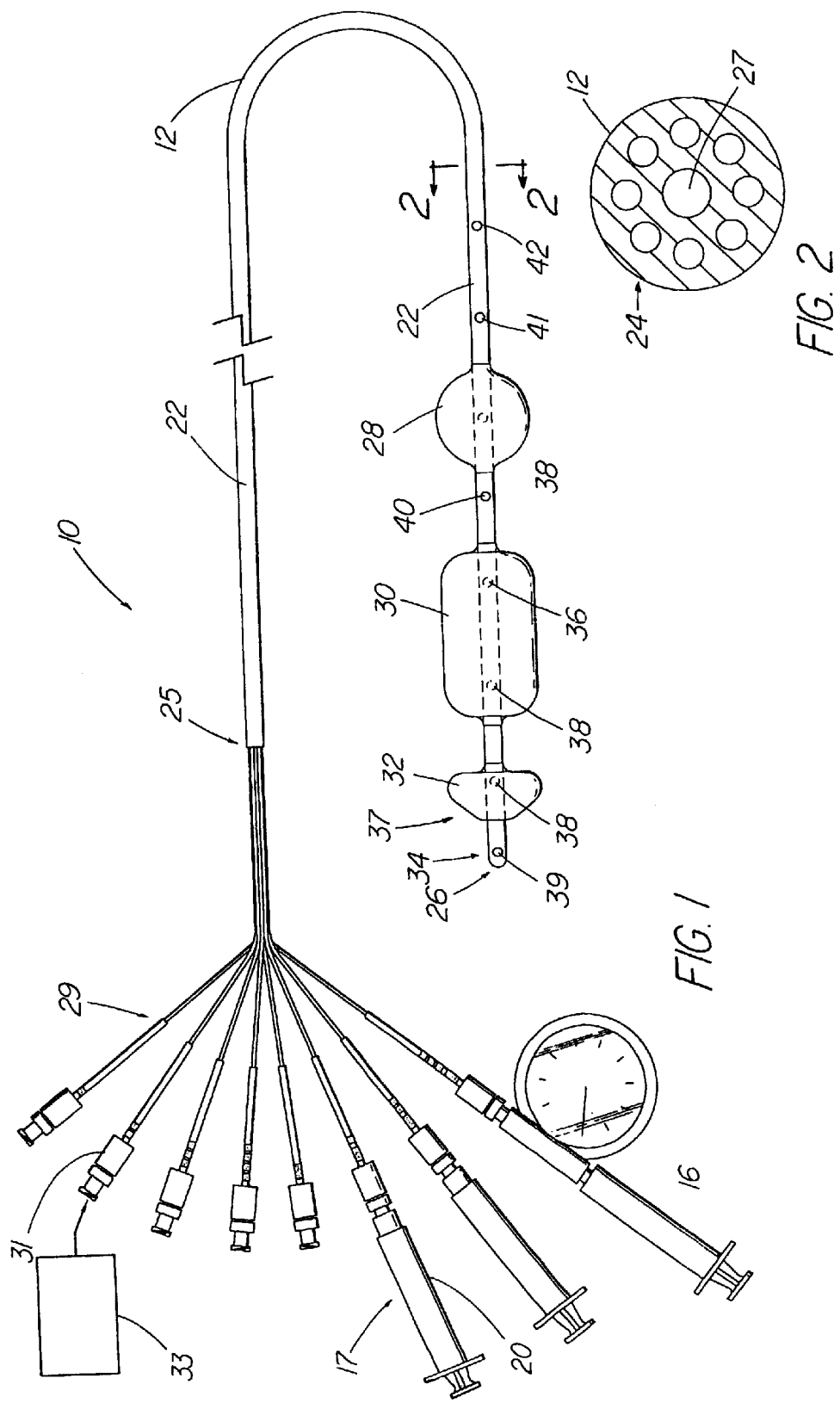

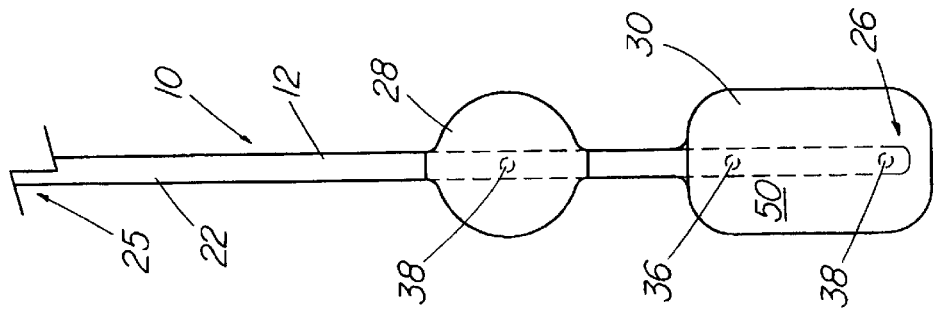
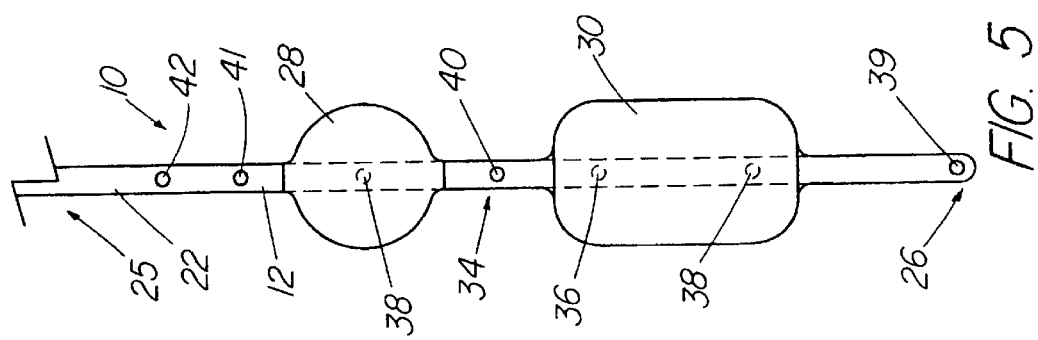
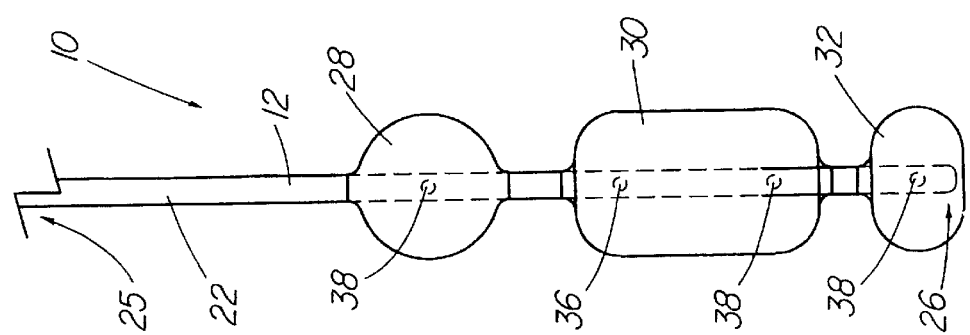

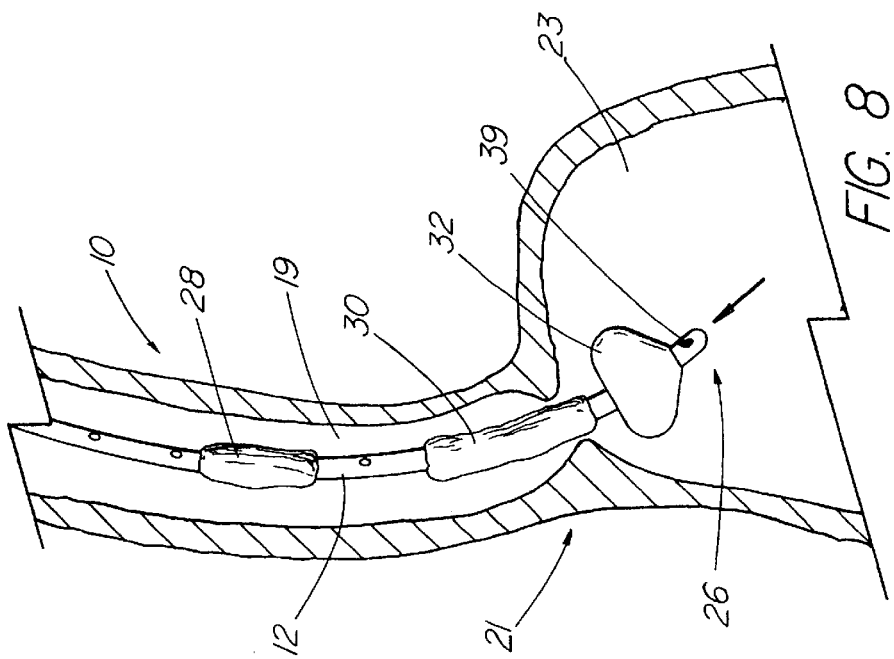
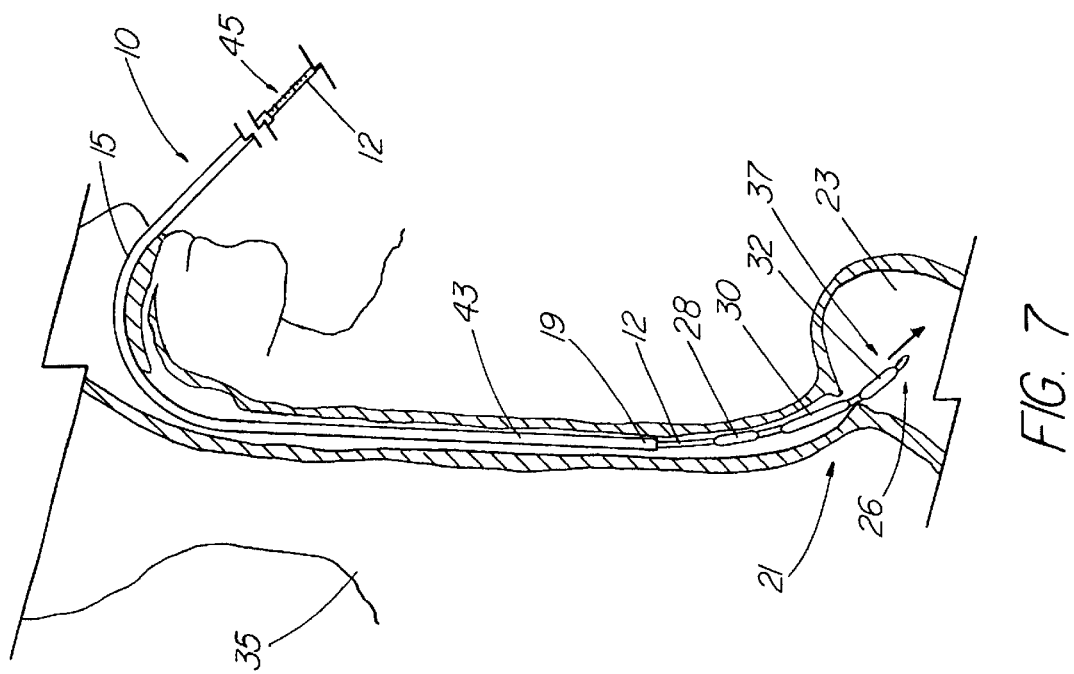

MANOMETRY APPARATUS FOR MEASURING ESOPHAGEAL SPHINCTER COMPLIANCE

RELATED APPLICATION INFORMATION

This application claims priority from U.S. Provisional Application Serial No. 60/192,172 filed Mar. 27, 2000.

TECHNICAL FIELD

The present invention relates to medical devices and more particularly to a method and apparatus for measuring the compliance or distensibility of the lower esophageal sphincter (LES) for use in the diagnosis of esophageal function.

BACKGROUND OF THE INVENTION

It is well known in the art to use esophageal and nasogastric catheters having balloon cuffs to measure the pressure within the esophagus. These devices have been used by and large to study the condition of the lungs and the blood pressure in and around the heart. For these purposes, it is desirous to measure pressure acting on the walls of the esophagus. Accordingly, an elastic balloon cuff, coupled to a suitable pressure transducer via a catheter, is inflated against the esophagus and the amount of pressure resistance is measured and used for various purposes in diagnosis. An elastic balloon is used because it can be distended outwardly to contact and conform with the region of interest in the esophagus.

Physicians also examine the condition of the gastroesophageal junction and in particular the lower esophageal sphincter (LES), which is an involuntary ring-like muscle separating the esophagus from the stomach. The LES rests in a closed position to shut off the end of the esophagus, and is relaxed when in the open state. However, the LES does not have the motility to open on its own, rather it opens briefly by normal physiological function of the esophagus during excitation of the inhibitory nerves of the esophagus. This most commonly occurs during peristalsis when the LES opens to allow food to pass from the esophagus to the stomach. Contracting nerves return the LES to its normally closed position.

Studying the LES is often necessary to diagnose various esophageal maladies and disorders such as gastroesophageal reflux disease, stricture, achalasia, diffuse esophageal spasm, esophageal cancer and dysphagia. These esophageal disorders affect the motility of the LES and thereby its ability to open and close normally.

Motility disorders of the esophagus, including those associated with systemic disease such as that of the connective tissue, are normally diagnosed using manometry, a procedure whereby a pressure-measuring instrument can assess function of the esophageal body by measuring peristaltic presence, propagation and vigor, or nonperistaltic contractions, as well as that of the upper and lower esophageal sphincters by measuring resting tone, timing and completeness of relaxation, and response to exogenous stimuli. The use of manometry is especially indicated in cases where more common esophageal disorders have been excluded after a barium radiograph or endoscopy evaluation, and it is often indicated for preoperative assessment of peristaltic function prior to antireflux surgery, and for placement of devices when the location depends on functional landmarks such as the lower esophageal sphincter (LES) located at the esophageal and gastric junction.

To obtain manometry data, the clinician typically measures the pressure exerted by the LES when constricted as well as when it is relaxed. This is typically done manometrically by inserting a sleeve with pressure transducers or other pressure recording devices into a patient's LES and measuring pressure as the patient swallows. The constricted and relaxed pressures are then compared to known values for a healthy LES (approximately 15–30 mm Hg constricted and 1–5 mm Hg relaxed). An LES with abnormal pressure values is then treated with drugs or a surgical procedure. A problem is that the measured pressure values of an LES may be normal despite the existence of dysphagia with or without an esophageal dysfunction. In this case, measuring the LES pressure does not provide information helpful in making a diagnosis. An additional disadvantage of manometry measurement is that it is a highly technical procedure that requires significant knowledge and precise methodology to produce valid results. Therefore, it has tended to be used more for physiological studies rather than a diagnostic tool in endoscopic or radiographic procedures. For example, manometry alone is insufficient to diagnose compliance disorders of the LES; the compliance of a sphincter is its ability to stretch and open properly in response to pressure applied to it from within to regulate the flow or movement of liquid or solid materials therethrough. For example, an important function of the LES is to prevent reflux of stomach acid into the esophagus, which not only causes discomfort to the sufferer, but can lead to a potentially serious condition known as Barrett's Esophagus. The ability to determine the degree of LES compliance is especially important during surgical procedures such as Nissen Fundoplication which involves wrapping the fundus of the stomach around the lower esophagus and suturing it into place to augment the biomechanical function of the LES. A quantitative measurement of compliance can provide an indication of whether the wrap is too loose or too tight, the latter resulting in an increased LES stricture that could cause difficulty in swallowing. If LES compliance can be assessed intraoperatively, the wrap can be adjusted, preventing the need for a second procedure to correct the problem. What is needed is a device that can be easily and reliably positioned for measuring compliance of the natural or reconstructed LES or gastroesophageal junction and to provide reliable data that can be readily interpreted to produce a quick assessment.

SUMMARY OF THE INVENTION

The inventor of the present invention has determined that, rather than the pressure exerted by the LES, the compliance (or distensibility) of the LES is determinative in diagnosing the LES dysfunction in certain medical and surgical cases. Simply measuring the pressure exerted by the LES is insufficient because it is possible for a dysfunctional LES to have proper pressure values due to the tone of the LES muscle, despite having abnormal compliance. Thus, to perform a useful diagnosis, it is necessary to isolate compliance from muscle tone, which can only be done by relaxing the LES and changing its diameter in a controlled manner to detect the change in pressure that is needed to change the LES diameter. However, as mentioned above, the LES is ordinarily constricted, relaxing only briefly to allow passage between the esophagus and stomach.

The foregoing problems are solved and a technical advance is achieved in a method and apparatus for maintaining the LES in a relaxed state and measuring the compliance of the LES in vivo. According to the invention, the LES is relaxed by distending the esophagus at a suitable position above the LES with a first extendable member, such as a balloon. The balloon is inflated to relax and trigger motility of the esophagus, thereby simulating a natural swallowing response that permits measurement the amount of resistance provided by the LES without the underlying tonic interference. As a result, a pressure reading can be obtained which is a more clinically relevant measurement of the compliance of the LES.

To measure compliance of the LES, a second extendable member, such as a non-elastic or non-distensible balloon (or bag), is inserted within the LES and filled at prescribed air volume increments via a catheter. A non-elastic balloon is infinitely compliant in that the pressure inside will not change until the volume of air being introduced into the balloon is at least equal to the volume of the balloon upon fabrication. The pressure within the bag is measured by a suitable gauge at each change in volume. A volume/pressure curve and/or data table is generated. These data can then be compared to established compliance norms for making a diagnosis. The pressure is measured by a measurement device, such as a gauge or pressure meter, reading the inflation lumen communicating with the non-elastic (intrasphincteric) balloon. By repeated inflations of the esophageal balloon using increasing volumes of air to obtain an increased physiologic response, a volume vs. pressure curve can be established for a particular patient that allows assessment of whether the LES is functioning properly. An alternative method of measuring pressure is to include a manometric pressure (recording) port within the intrasphincteric balloon that communicates with manometry sensors and transducers that are typically located at, or connected to, the proximal end of the compliance measurement catheter. While the extendable members of the present invention are typically balloons, they can assume any configuration (e.g., a basket) that can be manipulated to either obtain a pressure reading within the LES or extend outward to stimulate the esophagus to elicit the correct physiological response by sphincter.

In one aspect of the invention, the first and second balloons are mounted to an elongate member such as a surgical catheter defining a plurality of lumens. The first and second balloons are located along the catheter such that the intrasphincteric balloon is positioned in the LES (or gastroesophageal junction), while the first balloon is positioned in the esophagus. The lumens of the catheter communicate with an actuating mechanism or inflation means, such as a suitable air pump or syringe, and an apparatus for measuring pressure, such as a standard pressure gauge. The catheter lumens suitably terminate at ports within the bag and balloons, for filling the bag and balloons and measuring the intra-bag pressure.

In another aspect of the invention, the compliance balloon catheter further includes a distal, gastric balloon made of a compliant or non-elastic material that is inflated within the stomach so that the catheter can be partially withdrawn until the gastric balloon lodges below the LES, thereby correctly positioning the intrasphincteric balloon within the LES.

In still another aspect of the invention, manometric pressure ports are located at one or more points along the compliance balloon catheter for reading pressures found within the gastrointestinal tract. By comparing readings against known pressure gradient values that occur at various points within the esophagus and stomach, the compliance balloon catheter can be placed with some precision.

In still yet another aspect of the invention, a method for placement and use of a compliance balloon catheter in the LES is described in which the device is placed either transnasally or orally, and with or without the use of an endoscope. Referring to an embodiment that includes a gastric balloon, the compliance balloon catheter, preferably with the balloons deflated, is advanced such that at least the distal portion (defined herein as that portion of the catheter extending beyond the intrasphincteric balloon) is within the stomach. The gastric balloon is inflated and the catheter is partially withdrawn until the gastric balloon abuts the stomach wall and comes in contact with the LES. While the position of the compliance balloon catheter is maintained, the intrasphincteric balloon is inflated to determine baseline LES compliance. The esophageal balloon is then inflated. This balloon applies outward pressure on the esophagus at a suitable position above the LES, which causes the LES to relax through natural physiological functioning of the esophagus. To establish a volume-pressure relationship for evaluating sphincter compliance, the esophageal balloon is inflated with a series of increasing volumes of air and the resulting pressures produced by the sphincter acting upon the balloon are read by a pressure gauge attached to the inflation lumen of the intrasphincteric balloon, or by a manometry sensor and transducer attached to another catheter lumen separate from the intrasphincteric balloon inflation lumen. The data are used in a plot of volume vs. pressure with the slope of the curve providing an indication of LES compliance. This relation can then be compared against that of normative standards in making a diagnosis of the condition of the LES. After the final reading by the intrasphincteric balloon, all three balloons are deflated and the device is removed from the patient. The intrasphincteric balloon can be least partially deflated or maintained at the current inflation volume in between the series of inflations.

The intrasphincteric balloon can also be positioned within the LES manometrically. In this case, the catheter will include additional lumens terminating at ports located outside of the balloons. This allows the pressure at various locations within the esophagus to be measured and used to properly locate the balloon within the LES. Manometric measurements also can be used in combination with the gastric balloon for verification of correct placement.

Thus, the present invention provides a means for measuring in vivos the compliance of a relaxed LES. The pressure within the bag at various stages of inflation can be measured to establish a relation between volume and pressure. Predisposing the LES in a relaxed state removes the tension and tone of the muscle and allows the LES to distend without restriction from the muscle. This allows the compliance of the LES to be measured irrespective of muscle tone. Ultimately, this provides for a more effective means to diagnose certain esophageal dysfunctions.

Other objects and advantages will become apparent from the following description and drawings.

BRIEF DESCRIPTION OF THE DRAWINGS

Embodiments of the present invention will now be described by way of example with reference to the accompanying drawings, in which:

FIG. 1 depicts a front plan view of the apparatus of the present invention;

FIG. 2 depicts a cross-sectional view taken along line 2—2 of FIG. 1;

FIGS. 4–6 depict front plan views of various embodiments of the compliance balloon catheter of the present invention; and FIGS. 7–12 depict steps for measuring compliance of the lower esophageal sphincter using the embodiment of FIG. 1.

DETAILED DESCRIPTION

Figure 3:
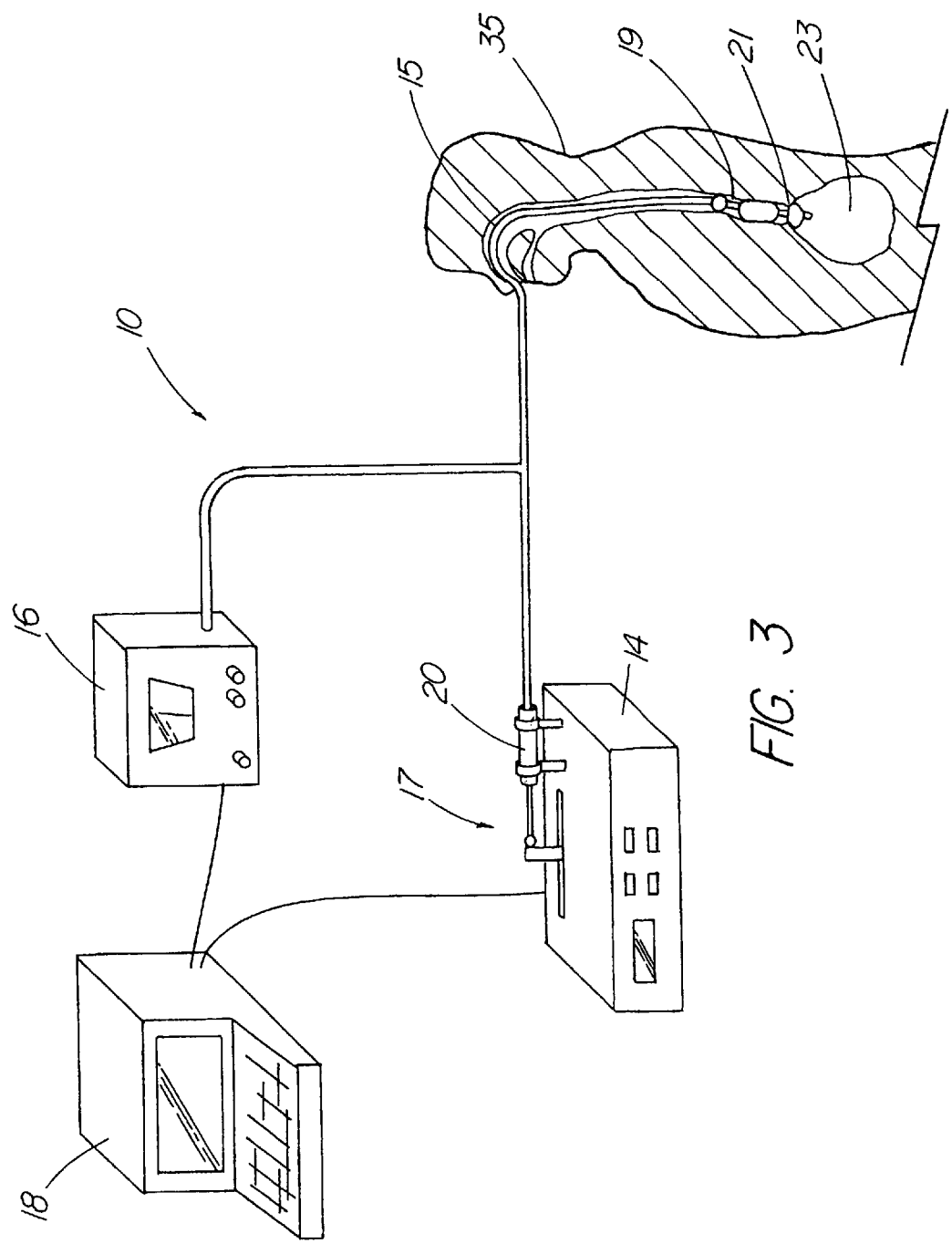
FIG. 3 depicts a schematic view the embodiment of FIG. 1 with exemplary instrumentation used with the present invention.

Referring to the drawings in detail, the LES compliance measurement apparatus of the present invention is referred to generally by numeral 10. A series of embodiments of the apparatus 10 are illustrated in FIGS. 1–6 which includes a sphincter compliance measurement catheter 12, such as a compliance balloon catheter, that comprises a length of tubing 22 having a first or distal end 26 and a second or proximal end 25. Disposed along the length of tubing 22 are a first extendable member 28, such as an inflatable balloon, with the first extendable member 28 being configured to expand and contact the walls of the esophagus, and a second extendable member 30, such as a non-elastic balloon or bag, that is placed in an intrasphincteric position for measuring the compliance of the LES. While the extendable members 28,30 of the illustrative embodiments are depicted as inflatable balloons, one skilled the art could appreciate that other expanding members, such as baskets or similar structures, that could be used to fulfill the function that is provided by the first (esophageal) balloon 28 and the second (intrasphincteric) balloon 30. For example, a basket with a strain gage could function as the second extendable member 30.

Optionally, a third extendable member 32, such as an inflatable balloon, can be located along the distal portion 37 of the compliance balloon catheter 12 to provide a means of correctly positioning the apparatus 10 such that the second balloon 30 is properly located within the sphincter to measure compliance. In the illustrative embodiment, the third (gastric) balloon 32, once inflated, allows the catheter to be gently pulled back from the stomach until the third balloon 32 contacts the stomach wall below the LES, thereby correctly positioning the first and second balloons 28,30. Alternatively, the third extendable member 32 can comprise a deflectable guide wire, a pigtail or umbrella-shaped device, etc. that is attached to, or deployed from the apparatus 10, such as via one of the plurality of lumens 24.

The compliance measurement catheter 12 of FIG. 1 is connectable to other instruments which both selectively inflate the series of balloons 28,30,32 and measure compliance pressure exerted by the LES, which permits calculation of a volume/pressure curve. FIG. 1 depicts one embodiment of a compliance balloon catheter 12 comprising a length of tubing 22 and three balloons 28,30,32 distributed therealong, each balloon being independently inflatable and deflatable. The tubing 22 is made of polyethylene, silicone, or another biocompatible polymer that offers good flexibility. The tubing 22 of the illustrative embodiment for LES compliance measurement is approximately 3–4 mm in diameter; however, a range of 2–5 mm is considered useful for LES compliance measurement, depending on the number of lumens required and whether the device is to be placed through an endoscope. The length of the catheter is variable depending on the specific embodiment with the proximal portion that extends from the section containing the balloons typically measuring 50–100 cm.

Referring now to FIG. 2, the compliance balloon catheter 12 includes a plurality of lumen 24, depicted in FIG. 2, defining separate passageways primarily available for inflation of the balloons 28,30,32 or the collection of manometry data. In the illustrative embodiment, an optional central lumen 27 is included which could be used for passage of a wire guide. Spaced about the length of the tubing 22, preferably 50–100 cm from the proximal end 25, is the esophageal balloon 28. The esophageal balloon 28 is sized to distend the esophagus when inflated. The illustrative esophageal balloon 28 is generally spherical with a diameter of 2.0–2.5 cm. Spaced another 5–7 cm from the esophageal balloon 28 is an intrasphincteric balloon 30, axially oblong is the illustrative embodiment, which is made of a non-elastic, non-distensible material, such as polyethylene teraphthalate (PET), a polyamide fabric, or some other polymer with the desired properties which can measure a force (i.e., LES compliance) acting against the balloon, once the full inflation volume has been attained. The intrasphincteric balloon 30 is typically 1–3 cm in diameter (more preferably 2–3 cm) and 4–6 cm long. Slightly below the intrasphincteric balloon 30 (e.g., 5–10 mm) is a transversely oblong gastric balloon 32 sized to catch stomach walls below the LES, preferably 2–5 cm in diameter and 4–5 cm wide. The esophageal 28 and gastric 32 balloons are typically made of an elastic material, such as latex or silicone; however, they may also be of the same (or other) non-elastic material as the intrasphincteric balloon 30. Preferably, the plurality of lumens 24 terminate either at their respective ports 34,36,38, or prior to the distal end 26 of the catheter, a typical exception being the central lumen 27, which can be used for a guide wire or other device, if desired.

FIGS. 1 and 3 depict examples of basic instrumentation and equipment used with the compliance measurement catheter 12. The basic elements are an actuating mechanism 17, which in the illustrative embodiments, serves to inflate the balloons 28,30,32; and a pressure meter 16 to measure the pressure exerted by the LES upon the intrasphincteric balloon 30. In FIG. 1, the actuating mechanism 17 comprises a plurality of syringes 20 that are connected to individuals connectors 29 extending from the proximal end 25 of the tubing, which in turn, feed dedicated lumens 24 that communicate with the inflation ports 38 within each balloon 28,30,32. A pressure meter (gauge) 16 is connected to the catheter 12 which communicates with a port 36 inside the intrasphincteric balloon 30 which is used to measure the pressure exerted on the balloon by the LES. In FIG. 3, the actuating mechanism 17 includes a metering pump 14 is used is used in combination with a pressure meter 16. The pump 14 and the pressure meter 16 are electrically coupled to a processor/data acquisition unit computer 18, such as a standard desktop computer, for collecting and processing pressure and volume data as described below. The metering pump 14 is preferably a medical metering pump, such as a Harvard pump or any pump with controllable metering known in the art, capable of accurately actuating a syringe 20 to pump prescribed air volume aliquots through the catheter 12. The pump 14 is in fluid communication with the pressure meter 16 via the catheter 12; however, certain pumps 14 are equipped with pressure measuring capabilities. In such an embodiment, a separate pressure meter 16 would be optionally available for manometric measurement if used in the placement of the apparatus 10. Besides the intrasphincteric balloon 30, the metering pump 14 can be connected to the esophageal and gastric balloons 28,32 as well to control their inflation. In FIG. 3, the pump 14, pressure meter 16 and computer 18 are shown as separate units, however, these items may be included in a single device. Moreover, it should be noted that the computer 18 is not required to practice the invention as the data may be recorded and calculations may be computed manually. As shown, the catheter 12 is inserted into the nasal passages 15 of a patient 35, into the esophagus 19, through the LES 21 and into the stomach 23; however, the catheter 12 may be inserted through the mouth if so desired.

In the illustrative embodiment of FIG. 1, a plurality of manometric pressure ports or sensors 34 are disposed along the compliance measurement catheter 12 for obtaining manometry data that may assist the clinician in placement of the apparatus 10. Generally, each manometric pressure port 34 is located at the terminus of a dedicated lumen in the compliance measurement catheter 12 that leads to a pressure meter 16 comprising a pressure sensor and transducer combination, usually a matched pair, that provides signals that are received and processed by a recording device. The manometry apparatus can consist of either water-perfused catheters with volume displacement transducers or strain gauge transducers with solid-state circuitry. A pneumohydraulic infusion pump (not shown) feeds the catheter. For the water-perfused system, typically a multi-lumen catheter is used in which each lumen terminates at a side-hole or sleeve channel within the esophagus and senses pressure at that position as the outflow of the perfusate encounters resistance. The strain gauge manometry system with solid-state electronics consists of a manometry probe with strain gauge transducers at fixed positions along its length. The device is plugged into a unit containing the electronics which is, in turn, connected to a recorder. Alternatively, the pressure sensors and/or transducers 33 can be located within the tubing of the catheter 22, with wires extending to an external or integral unit for recording and/or analyzing the data collected via the manometric pressure port 34.

Referring now to FIG. 1, spaced slightly proximal to the esophageal balloon 28 are a first and second esophageal manometric pressure ports 41,42 for obtaining manometric readings within the esophagus. The pressure ports 34 are located to be below the upper esophageal sphincter (not shown) when the catheter 12 is inserted in the esophagus. The catheter 12 includes additional manometric pressure ports 34. A suprasphincteric manometry port 40 is located between the esophageal balloon 28 and the intrasphincteric balloon 30 and a fourth port, the gastric manometry port 39, is located distal of the gastric balloon 32, each connected to a pressure transducer 33 or the pressure meter 16 via a separate lumen 24. The catheter 12 also includes a measurement pressure port 36 within the intrasphincteric balloon 30 connected to the pressure meter 16 via dedicated lumen 24.

As indicated, manometric pressure port 34 can be used to make pressure measurements within the gastrointestinal tract. Due to normal differences in pressure readings that occur within the esophagus, the sphincters, and the stomach, manometry has been used as a tool in assessing motility of the esophagus and other potential physiologic markers for diagnostic purposes. The gastric manometric pressure port 39, located near the distal end 26 of the compliance balloon catheter 12, would normally measure 5–10 mm Hg of pressure when properly located within the stomach, whereas a pressure reading below 5 mm Hg would indicate that the distal end 26 of the device had not been completely advanced from the esophagus into the stomach. The suprasphincteric manometric pressure port 40, located between the intrasphincteric balloon 30 and the esophageal balloon 28, provides a pressure reading above the LES, while one or more esophageal manometric pressure ports 41,42 measure pressures found higher in the esophagus.

FIGS. 7–12 depict a method of placing the compliance balloon catheter 12 of FIG. 1 within the LES 21 of a patient. The compliance balloon catheter 12 can be inserted transnasally, e.g., through an endoscope 43 as depicted in FIG. 7, or it can be introduced orally. Placement using an endoscope 43 is optional. Optional depth markers 45 can be added to the catheter tubing 22 to aid in placement of the compliance balloon catheter 12. For example, it is important not to inflate the gastric balloon 32 before it is completely inside the stomach 23. These markers 45, which can be useful when used with or without an endoscope, can comprise printed numerical or other type of indicia corresponding to the distance to a certain distal point on the compliance balloon catheter, or they can indicate one or more preferred zones corresponding to the desired position of balloon deployment. Verification of position can also be obtained by reading from the gastric manometry port 39 at the near the distal end 26 of the compliance balloon catheter 12 to determine that the pressure reading lies within the expected values found in the stomach. Conversely, the suprasphincteric port 40 and esophageal ports 41,42 can be used to read whether or not the pressures are appropriate for the esophagus.

Figure 9:
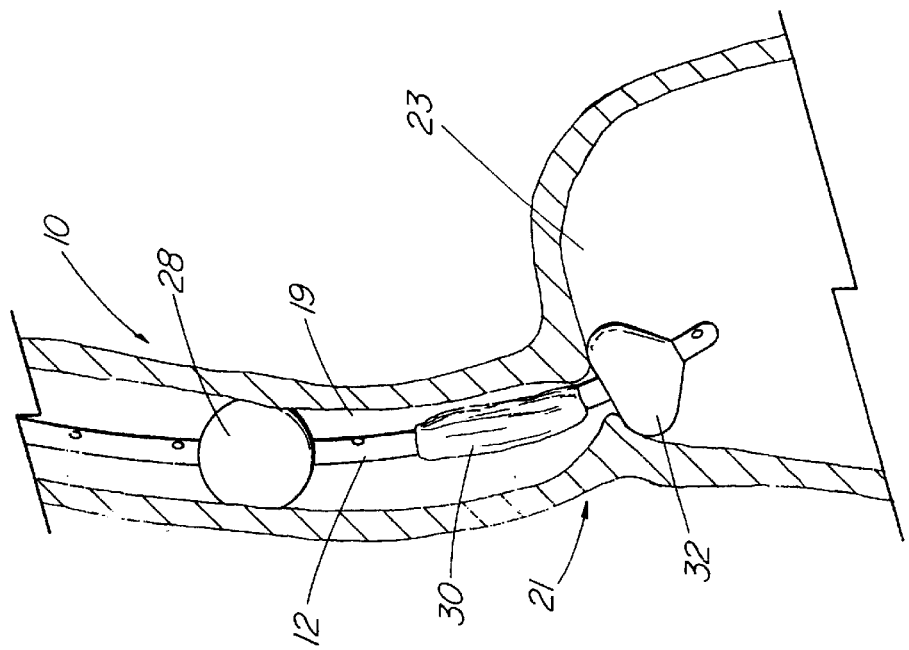
Figure 10:
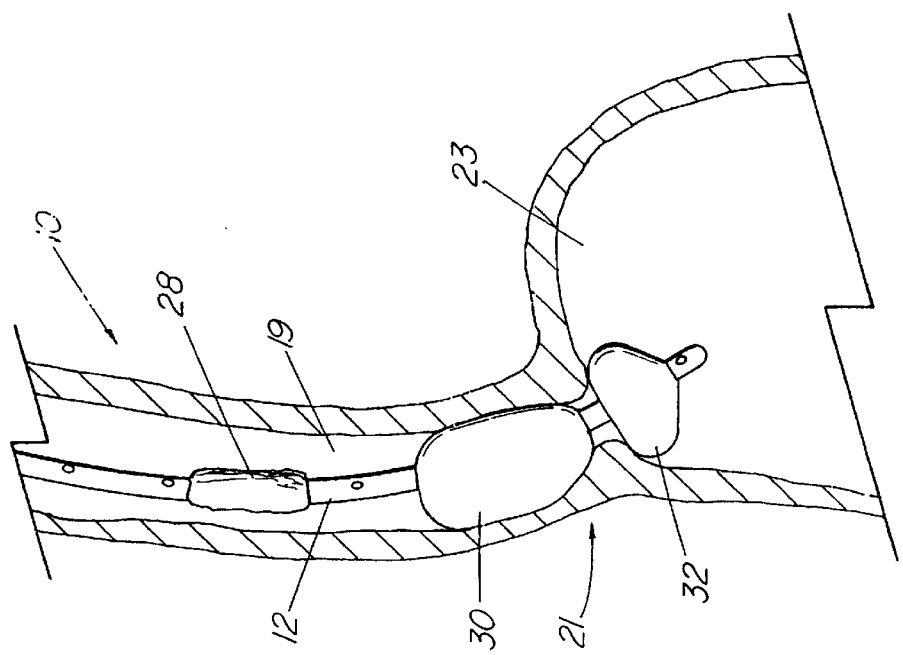

Referring to FIGS. 1 and 3, the apparatus 10 is used by inserting the distal end 26 of the catheter 12 through a patient's nasal passages 15 and into the esophagus 19 so that the distal end 26 travels through the LES 21. The preferred embodiment of the present invention provides multiple means for properly locating the catheter 12 within the esophagus 19 so that the intrasphincteric balloon 30 is disposed within the LES 21. Regardless of the method of placement used, the distal end 26 of the catheter compliance balloon catheter 12 is advanced (preferably with the balloons 28, 32 and 30 collapsed) such that it traverses the esophagus 19 and LES 21. In the illustrative embodiment of FIG. 7, which includes a gastric balloon 32, the distal portion 37 of the catheter, including the gastric balloon 32, is advanced beyond the LES 21 and into the stomach 23 where the gastric balloon 32 is inflated, using a syringe or pump, as shown in FIG. 8, to become a positional marker for properly locating the non-elastic intrasphincteric balloon 30 within the LES 21. The catheter 12 and inflated gastric balloon 32 are gently withdrawn until the gastric balloon 32 abuts the stomach wall as shown in FIG. 9. The gastric balloon 32 must be sufficiently large such that the distal balloon 15, once inflated, will not readily pull through the LES.

Alternatively, the catheter 12 can be positioned manometrically by monitoring the pressure values of the air entering through the manometric pressure ports 34 and comparing these pressure values to standard pressures at various locations within the esophagus 19 and stomach 23. Another alternative positioning technique that can be used with the present invention is to coat portions of the catheter 12, such as the intrasphincteric balloon 30, with a suitable x-ray opaque material known in the art, and passing low-level x-rays through the patient's torso. The coated portion(s) of the catheter 12 will be visible in a resulting static or motion x-ray (fluoroscopic) image and its location then can be determined. Another alternative would be to create an ultrasonic reflective surface on the catheter 12 or one of the balloons, such that ultrasonic imaging can be used to position the catheter 12. As depicted in FIG. 9, once the gastric balloon 32 has been inflated, the intrasphincteric balloon 30 is also inflated, as depicted in FIG. 9, to measure the baseline tone of the LES 21 while at rest.

Figure 11:
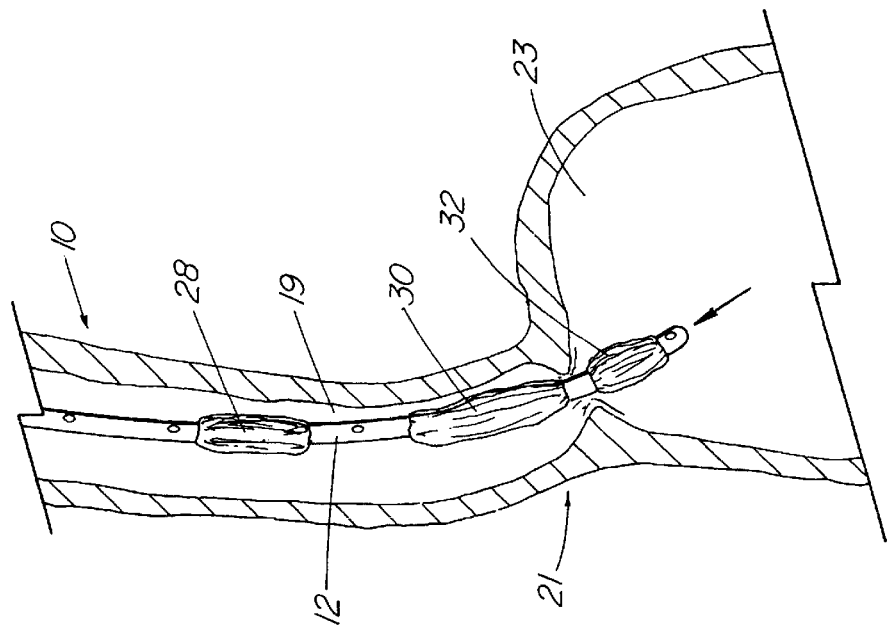
Figure 12:
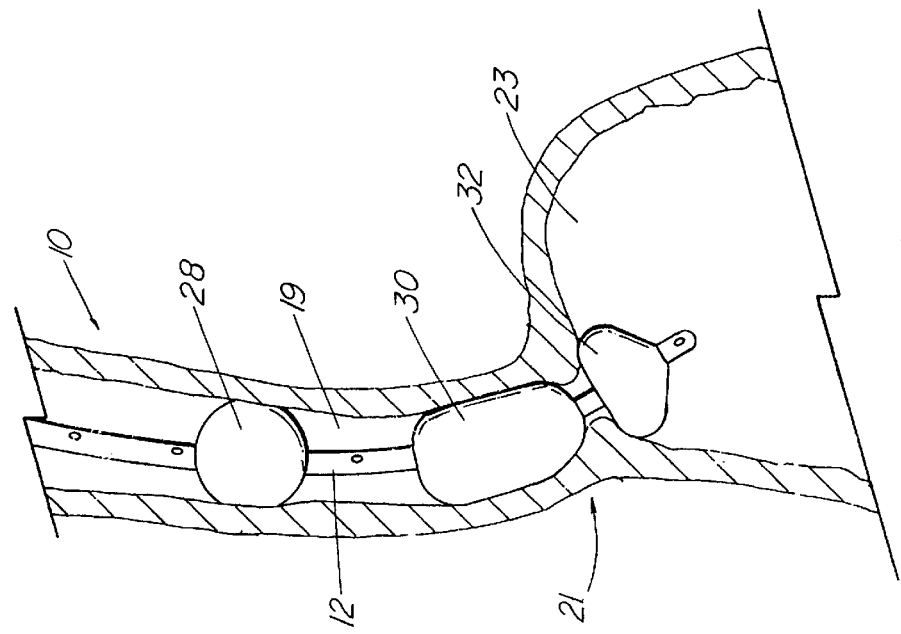

Referring to FIG. 11, the intrasphincteric balloon 30, now properly positioned within the LES, is inflated using either a syringe 20 or the metering pump 14 and syringe 20 of FIG. 3. By way of the example shown in FIG. 3, the pump 14 is activated at prescribed increments to meter air through the syringe 20 and appropriate lumen 24 into the intrasphincteric balloon 30. It is optional whether to partially deflate the intrasphincteric balloon 30 in between measurements or merely increase the volumes in steps. The incrementally increasing volume inflations can be done in any reasonable manner, but a suggested interval for the present embodiment would include regular 2–5 ml increases in volume until the balloon capacity has been reached as shown in FIG. 11. Generally, the pressure within the intrasphincteric balloon 30 is measured by the pressure meter 16 and recorded by the computer 18 for each volumetric increment. These data can then be processed to produce a volume/pressure curve illustrating the compliance of the LES 21.

As is understood by those skilled in the art, if the intrasphincteric balloon 30 was removed from the esophagus 19 so that it was not externally constrained, the theoretical internal pressure would be zero. The internal pressure would remain zero until the intrasphincteric balloon 30 was filled. Because the intrasphincteric balloon 30 is non-elastic, the internal pressure then would rise quickly until the intrasphincteric balloon 30 could no longer compress the internal air, and it would then burst. A volume-pressure curve in this case would be flat until the intrasphincteric balloon 30 was filled, after which it would ramp rapidly upward. If the pressure within the intrasphincteric balloon 30 was measured without relaxing the LES 21 (i.e., without inflating the esophageal balloon 28), the LES 21 would constrict the intrasphincteric balloon 30 along the inner diameter of the intrasphincteric balloon 30. To inflate, the internal pressure must be greater than the force acting on the intrasphincteric balloon 30 from the muscle tone and tissue of the LES 21. This creates a much steeper volume/pressure curve.

Relaxing the LES 21, by inflating the esophageal balloon 28, removes the tension and tone of the muscle and allows the LES 21 to distend without restriction by the muscle. Only its muscle tissue acts as an impediment to the outward expansion of the intrasphincteric balloon 30 and thus the LES 21 is not forcefully constricting the intrasphincteric balloon 30. Yet, since the LES 21 is not infinitely compliant (as is external air), the pressure within the intrasphincteric balloon 30 will be at some value above the theoretical zero. This value will increase as the volume of the intrasphincteric balloon 30 increases in part due to compression of the air, but primarily because of the LES 21. The internal pressure will increase gradually until the intrasphincteric balloon 30 is full after which the pressure increases dramatically, as described above. Thus, the volume/pressure curve of the relaxed LES 21 will be much flatter than that of a resting LES 21. This curve represents a more clinically relevant indiction of LES compliance because it eliminates the effects of muscle tone. Using this technique, while the LES 21 is relaxed, two or more pressure data points can be measured as the LES 21 is distended. In other words, for each change in balloon volume (LES distention), the change in pressure can be measured while the LES 21 is in a constant state (relaxed) without the dynamic affect of muscle tone. Thus, this technique and apparatus allows a physician to isolate and study LES 21 compliance irrespective of musculature, allowing for a more precise understanding of the condition of the LES 21.

Using a hypothetical example of the present method, the esophageal balloon 28 is inflated to trigger a motility response and relax the esophagus. The intrasphincteric balloon 30 is inflated inside the LES using 5 ml of a fluid such as air. The balloon encounters resistance from the LES, causing the pressure gauge 16 to read a pressure of 2 mm Hg. The esophageal balloon 28 is either given 5 ml of additional air or deflated and then reinflated with 10 ml, which invokes increased resistance resulting in a reading of 4 mm Hg. The esophageal balloon 28 must be in the inflated state during each reading. Further increases in volume result in corresponding increases in pressure that usually are not linear. For example, a 30 ml balloon may reach a maximum pressure of 10 mm Hg in a normal LES. However, in an abnormally non-compliant sphincter, such as if a Nissen Fundoplication wrap of the LES is made too tight, the pressure reading will be higher, e.g., 17 mm Hg. By comparing the values and slopes of the curves preoperatively and intraoperatively or postoperatively, adjustments can be made such that the LES compliance can be readjusted.

After the last inflation, each of the balloons 28,30,32 is deflated (FIG. 12) and the compliance balloon catheter 12 is removed from the patient. If the fundoplication wrap tightness is to be readjusted or another later measurement is needed for some other reason, the compliance balloon catheter 12 may be temporarily left in place and redeployed for additional measurement, or at least partially withdrawn, then repositioned and redeployed later. While the present embodiment is highly useful for establishing LES compliance pre- and intraoperatively, it can also function as a means for evaluating patients with a variety of potential conditions such as acid reflux disease, a hypotensive LES, or non-specific motility disorders such as difficulty in swallowing.

To study the concept of measuring LES compliance in vivo the applicant conducted at study on dogs using the present invention and technique. The study included measuring in vivo the compliance of a relaxed LES according to the present invention, a resting LES and an LES injected with atropine, a muscle relaxant. Five unanesthetized dogs were studied in two stages. As a measure of preserved sphincter integrity, LES pressure was determined by a sleeve before and after maximum distention of an infinitely compliant barostat bag (2 cm diameter, 10 cm length, 30 ml volume), which was subsequently also used to study LES compliance. The above mentioned bag was repositioned across the LES through a chronic esophagostomy and using a Harvard pump the volume/pressure curve was determined for randomly injected aliquots of 5–35 ml of air. Transsphincteric positioning for all catheters was confirmed manometrically. The volume/pressure curve was as determined for resting LES, completely relaxed LES (by inflating a separate 2.5 cm balloon in mid esophagus) and following IV injection of 4 mg atropine. Compliance was calculated as $\Delta V/\Delta P$ for each volume aliquot. The results were that LES pressure following maximum bag distention (33=4 mm Hg), was similar to pre-distention values (30=2 mm Hg). A direct correlation between volume of injected air and intra-bag pressure was observed for all tested conditions. LES compliance during complete relaxation was significantly higher compared to resting and post-atropine states (see Table). LES compliance following atropine injection was significantly higher than in the resting state. In conclusion, it was found that LES compliance can be safely measured in vivo using a 2 cm infinitely compliant bag. Furthermore, compliance of the LES is influenced by its excitatory and inhibitory innervation. Finally, LES compliance is affected by its degree of stretch. Using this technique and apparatus, the muscle tone of the LES was greatly reduced or eliminated, putting and maintaining the LES in a suitable state for measuring compliance. The study indicates that compliance of the relaxed LES is greater than that of the post-atropine LES which is greater than that of the resting (closed) LES. The data was as follows:

| LES Compliance at Incremental Volume Ranges | | | | | | |
|---|---|---|---|---|---|---|
| | 5 to 10 | 10 to 15 | 15 to 20 | 20 to 25 | 25 to 30 | 30 to 35 |
| control | 2.6 ± 0.2 | 1.9 ± 0.2 | 1.5 ± 0.1 | 1.6 ± 0.2 | 1.4 ± 0.2 | 1.4 ± 0.3 |
| atropine | 4.5 ± 0.1* | 3.6 ± 0.3* | 2.4 ± 0.3* | 1.7 ± 0.3 | 1.3 ± 0.2 | 1.5 ± 0.3 |
| relaxed | 6.3 ± 0.3 | 5.6 ± 0.3 | 5.0 ± 0.2 | 5.5 ± 0.3 | 3.6 ± 0.2** | 1.2 ± 0.2 | note: asterisk(s) indicate that the value is significantly different ($p < 0.05$) from the control value for that volume.

In a later study of ten human patients using a device of the present invention having a 2 cm diameter, 30 ml intrasphincteric balloon and a 2.5 cm esophageal balloon, it was found that LES compliance could be safely measured. Furthermore, it was found that LES compliance was influenced by phases of respiration and increased by esophageal distention/LES relaxation. The different respiration phases included normal breathing, end-inspiration breath hold, mid-inspiration breath hold, each with and without esophageal distention following 12 $\mu$g/kg IV atropine x3. A direct correlation between intrasphincteric balloon volume and pressure was observed for all test conditions. LES compliance with balloon-induced relaxation was significantly higher compared to that without balloon distention and post atropine status. Compliance was found to be highest during normal breathing, followed by mid-inspiration and end-inspiration breath holds.

FIGS. 4–5 illustrate alternate embodiments of the catheter of the present invention. The common elements with the first illustrative embodiment of FIG. 1 include, the tubing 22, the esophageal balloon 28, intrasphincteric balloon 30, their associated inflation ports 38 and the 36 pressure measurement port. The embodiment shown in FIG. 4 includes tubing 22 with at least four lumens 24 as well as a gastric balloon 32. This embodiment provides for only mechanically positioning via the gastric balloon 32 as there are no manometric ports. Conversely, the embodiment shown in FIG. 5 does not include a gastric balloon 32 and therefore uses manometric positioning via the manometric pressure ports 34 in the tubing 22 and five of the at least seven lumens 24. Finally, in the embodiment of FIG. 6, the tubing 22, which requires no more than three lumens 24, terminates within the intrasphincteric balloon 30 and includes no gastric balloon or manometric ports. This embodiment is positioned using a well known imaging technique, such as x-ray or fluoroscopy to detect an x-ray opaque coating 50 on the outer surface of the intrasphincteric balloon 30, or ultrasound imaging to detect an ultrasonically reflective surface disposed about a portion of the apparatus. It should also be noted that the distal end of the intrasphincteric balloon can be modified such that when the balloon is partially or fully inflated, it can help with positioning within the LES from above during introduction.

Illustrative embodiments of the present invention have been described in considerable detail for the purpose of disclosing a practical, operative structure whereby the invention may be practiced advantageously. The designs described herein are intended to be exemplary only. The novel characteristics of the invention may be incorporated in other structural forms without departing from the scope of the invention. For example, the present invention can be modified to measure the compliance of sphincter found elsewhere in the body, e.g., the anal sphincter, where two extendable members, such as balloons, can be used in tandem to elicit the proper physiologic response for obtaining a measurement of sphincter compliance.

What is claimed is:

1. An apparatus for measuring the compliance of a sphincter of a mammal comprising:
    a compliance measurement catheter further comprising a length of tubing having a first end, a second end, and at least one lumen extending at least substantially therealong;
    a first extendable member disposed about the length of tubing, the first extendable member sized and configured to such that it is sufficiently extendable to contact the walls of a body lumen proximate the sphincter and cause the sphincter to enter a transient state of relaxation; and
    a second extendable member located proximate to the first extendable member along the length of tubing, the second extendable member comprising an inflatable member of a material that is substantially non-elastic when the full available volume of the inflatable member is inflated with a fluid, the inflatable member being sized and configured to contact the inner walls of the sphincter in a manner such that the force of the sphincter against the inflatable member results in pressure changes within the inflatable member that are measurable by a manometric measurement port disposed therein, the measurable pressure changes being usable for assessing compliance of the sphincter.

2. The apparatus of claim 1 wherein the first extendable member comprises an inflatable esophageal balloon disposed along the length of tubing such that the esophageal balloon is located in the esophagus of the mammal when the second extendable member is placed within the lower esophageal sphincter.

3. The apparatus of claim 1, further comprising a third extendable member located distal of the first and second extendable members and adapted for correctly positioning the second extendable member within the sphincter following deployment of the third extendable member within the stomach of the mammal.

4. The apparatus of claim 3, wherein the third extendable member comprises an inflatable gastric balloon.

5. The apparatus of claim 1, wherein the length of tubing further includes at least one manometric measurement port disposed therealong, the at least one manometeric measurement port so positioned for measuring the internal pressure found within at least one of a group that includes the esophagus, the lower esophageal sphincter, and the stomach when the apparatus in being placed within the body of the mammal.

6. The apparatus of claim 5, wherein the apparatus includes a plurality of manometric measurement ports, the plurality of manometric measurement ports including at least one disposed about the distal end of the apparatus and at least one generally disposed adjacent the first extendable member.

7. The apparatus of claim 1, further including at least one pressure measurement device.

8. The apparatus of claim 7, further comprising a data processor adapted to analyze data obtained from the second expandable member to determine the sufficiency of the compliance of the sphincter.

9. The apparatus of claim 1, wherein the compliance measurement catheter includes a pattern of indicia distributed therealong for indicating correct placement of the second extendable member within the sphincter of the mammal.

10. An apparatus for measuring the compliance of a sphincter of a mammal comprising:

a compliance measurement catheter further comprising a length of tubing having a first end, a second end, and a plurality of lumens extending at least substantially therealong;

a first balloon disposed about the length of tubing; and a second balloon located proximate to the first balloon along the length of tubing, the second balloon comprising a substantially non-elastic material and is sized and configured such that the second extendable member is inflatable to at least substantially contact the inner walls of the sphincter, the second balloon further comprising at least one manometric measurement port disposed therein for obtaining a measurement of compliance of the sphincter when the compliance measurement catheter is connected to a measurement device, the first balloon being positioned along the compliance measurement catheter such that when the second balloon is located within the sphincter, the first balloon resides in an adjacent body lumen, the first balloon being adapted to contact the inner surface of the adjacent body lumen when manipulated by an operator, thereby triggering a physiologic response by the adjacent sphincter.

11. The apparatus of claim 10, wherein the second balloon is sized and configured for placement in a lower esophageal sphincter of a human patient, the second balloon adapted to be inflated while inside the lower esophageal sphincter using an amount of a fluid such that a pressure reading results from the degree of compliance of the lower esophageal sphincter when the apparatus is connected to a pressure measurement device, whereby increasing amounts of fluid produce a series of pressure readings that can be used to indicate sufficiency of the compliance of the sphincter.

12. The apparatus of claim 1, wherein the first balloon is positioned within the esophagus of the patient when the intrasphincteric balloon is located within the lower esophageal sphincter.

13. The apparatus of claim 11, wherein the second balloon is generally oblong in shape.

14. The apparatus of claim 12, further comprising a third balloon located distal of the first and second balloons and adapted for correctly positioning the second balloon within the lower esophageal sphincter following deployment of the third balloon within the stomach of the patient and against the stomach wall proximate the LES.

15. The apparatus of claim 10, wherein the length of tubing further includes at least one manometric measurement port disposed therealong, the at least one manometric measurement port so positioned for measuring the internal pressure found within at least one of a group that includes the esophagus, the lower esophageal sphincter, and the stomach when the apparatus in being placed within the body of the mammal.

16. The apparatus of claim 15, wherein the apparatus includes a plurality of manometric measurement ports includes at least one disposed about the distal end of the apparatus for measurement of pressure within the stomach and at least one generally disposed adjacent the first balloon member for measurement of pressure within the esophagus.

17. An apparatus for measuring the compliance of a sphincter of a mammal comprising:

a compliance measurement catheter further comprising a length of tubing having a first end, a second end, and a plurality of lumens extending at least substantially therealong;

a first balloon comprising an elastic material, the first balloon disposed about the length of tubing;

a second balloon comprising a non-elastic material and having a generally oblong shape, the second balloon located proximate to the first extendable member along the length of tubing;

a third balloon located distal of the first and second balloons and adapted for correctly positioning the second balloon within the lower esophageal sphincter following deployment of the third balloon within the stomach of the patient;

a plurality of manometric measurement ports disposed along the length of the tubing adapted to obtain pressure measurement within the esophagus and the stomach, the second extendable member being sized and configured such that the second extendable is inflatable to at least substantially contact the inner walls of the sphincter, the second balloon further adapted for obtaining a measurement of compliance of the sphincter when the compliance measurement catheter is connected to a measurement device, and the apparatus configured with the first balloon being positioned along the catheter such that when the second balloon is located within the sphincter, the first balloon resides in an adjacent body lumen, the first extendable member being adapted to contact the inner surface the adjacent body lumen when manipulated by an operator, thereby triggering a physiologic response by the adjacent sphincter.

* * * * *